US011726044B2

United States Patent
Kraemer et al.

(10) Patent No.: US 11,726,044 B2
(45) Date of Patent: Aug. 15, 2023

(54) METHOD OF MONITORING AN OPERATION OF DETECTION OF AN ANALYTE IN A LIQUID SAMPLE

(71) Applicant: Roche Diagnostics Operations, Inc., Indianapolis, IN (US)

(72) Inventors: Reinhold Kraemer, Peissenberg (DE); Michael Kuehnl, Munich (DE); Uwe Mertsch, Starnberg (DE); Marion Borchers, Munich (DE)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 611 days.

(21) Appl. No.: 16/739,236

(22) Filed: Jan. 10, 2020

(65) Prior Publication Data

US 2020/0150046 A1    May 14, 2020

Related U.S. Application Data

(63) Continuation of application No. PCT/EP2018/069937, filed on Jul. 23, 2018.

(30) Foreign Application Priority Data

Aug. 1, 2017    (EP) .................................... 17184342

(51) Int. Cl.
*G01N 21/69*    (2006.01)
*G01N 21/47*    (2006.01)
(Continued)

(52) U.S. Cl.
CPC ............. *G01N 21/69* (2013.01); *G01N 21/47* (2013.01); *G01N 21/76* (2013.01); *G01N 27/416* (2013.01);
(Continued)

(58) Field of Classification Search
CPC ............... G01N 21/76; G01N 2458/30; G01N 33/5438; G01N 33/582; G01N 27/30;
(Continued)

(56) References Cited

U.S. PATENT DOCUMENTS 5,238,808 A    8/1993 Bard et al.
5,322,597 A    6/1994 Childs et al.
(Continued)

FOREIGN PATENT DOCUMENTS

AU    2003302263 A1 *  7/2004 .......... B01J 19/0046
EP        0658760 A1 *  6/1995
(Continued)

OTHER PUBLICATIONS

International Search Report dated Aug. 24, 2018, in Application No. PCT/EP2018/069937, 2 pp.
(Continued)

*Primary Examiner* — Michael P Stafira
(74) *Attorney, Agent, or Firm* — Woodard, Emhardt, Henry, Reeves & Wagner, LLP

(57) ABSTRACT

A method of monitoring detection of an analyte in a liquid sample using a measuring cell, the measuring cell comprising a working electrode for excitation of electrochemiluminescence in the liquid sample, an optical detector for detecting the excited electrochemiluminescence, the excitation and detection being performed in an measurement cycle, the measurement cycle comprising transporting the liquid sample via a transport path to the working electrode using a support liquid, the method comprising: coupling light of a light source into the transport path during part of the measurement cycle, the transport path forming a light guide between the light source and the optical detector, detecting the coupled light by the optical detector, analyzing the detected light for a gas bubble in the transport path, provid-
(Continued)

ing a measurement state if the result of the analysis deviates from a target state regarding the presence of a gas bubble in the transport path.

25 Claims, 6 Drawing Sheets

(51) Int. Cl.
*G01N 21/76* (2006.01)
*G01N 27/416* (2006.01)
*G01N 33/543* (2006.01)
*G01N 21/84* (2006.01)

(52) U.S. Cl.
CPC ... *G01N 33/543* (2013.01); *G01N 2021/4726* (2013.01); *G01N 2021/8411* (2013.01); *G01N 2458/30* (2013.01)

(58) Field of Classification Search
CPC .... G01N 33/543; G01N 33/533; G01N 21/69; G01N 33/569; G01N 33/76; G01N 2021/0346; G01N 21/0303; G01N 21/03; G01N 21/66; G01N 33/532; G01N 33/56911; G01N 33/57434; G01N 33/57484; G01N 2800/52; G01N 1/10; G01N 2021/054; G01N 21/05; G01N 2333/70578; G01N 2800/60; G01N 33/53; G01N 33/57449; G01N 33/6893; G01N 33/54366; G01N 21/6428; G01N 21/6486; G01N 33/523; G01N 33/574; G01N 2021/4726; G01N 2021/8411; G01N 21/47; G01N 27/416; G01N 2021/6482; G01N 2021/7786; G01N 21/645; G01N 21/7703; G01N 2333/90241; G01N 2333/90245; G01N 33/57488; G01N 2021/6432; G01N 21/6408; G01N 2333/705; G01N 33/57419; G01N 33/68; G01N 2400/40; G01N 2570/00; G01N 27/745; G01N 33/50; G01N 33/54326; G01N 33/566; G01N 33/6842; G01N 2021/772; G01N 2021/773; G01N 2021/775; G01N 2021/7753; G01N 21/8483; G01N 27/44704; G01N 33/48; G01N 33/57407; G01N 33/6863; G01N 35/00; G01N 1/31; G01N 1/405; G01N 2035/00108; G01N 2035/00148; G01N 2035/00247; G01N 21/64; G01N 21/648; G01N 2201/06113; G01N 2201/062; G01N 27/327; G01N 27/3276; G01N 27/447; G01N 27/44721; G01N 27/44791; G01N 27/74; G01N 33/14; G01N 33/487; G01N 33/49; G01N 33/5002; G01N 33/5076; G01N 33/5302; G01N 33/54346; G01N 33/54386; G01N 35/00029; G01N 35/0098; G01N 2035/00158; G01N 2333/475; G01N 2333/91177; G01N 2333/914; G01N 2800/10; G01N 33/5308; G01N 33/74; G01N 35/00069
See application file for complete search history.

(56) References Cited

U.S. PATENT DOCUMENTS

| | | |
|---|---|---|
| 5,583,635 A | 12/1996 | Miura |
| 5,779,976 A * | 7/1998 | Leland ................. G01N 33/582 422/52 |
| 5,960,129 A | 9/1999 | Kleinschmitt |
| 6,599,473 B1 | 7/2003 | Egger et al. |
| 9,952,237 B2 * | 4/2018 | Fournier ............... B01L 3/5085 |
| 2001/0008612 A1 * | 7/2001 | Liljestrand ............ G01N 21/76 422/52 |
| 2005/0106652 A1 * | 5/2005 | Massey .................. G01N 33/76 435/6.12 |
| 2006/0042963 A1 | 3/2006 | Kaltenbeck et al. |

FOREIGN PATENT DOCUMENTS

| | | | |
|---|---|---|---|
| EP | 2620764 A1 * | 7/2013 | ......... G01N 21/6408 |
| EP | 2816345 A1 * | 12/2014 | ............ G01N 21/66 |
| JP | S61-181953 A | 8/1986 | |
| JP | H06-273403 A | 9/1994 | |
| JP | H11-223596 A | 8/1999 | |
| JP | 2011-158258 A | 8/2011 | |
| WO | 1986/002734 A1 | 5/1986 | |
| WO | 1990/011511 A1 | 10/1990 | |
| WO | 1999/039206 A1 | 8/1999 | |
| WO | WO-2011071772 A2 * | 6/2011 | ............ B01L 3/5027 |
| WO | 2013/173524 A2 | 11/2013 | |
| WO | 2014/202298 A1 | 12/2014 | |

OTHER PUBLICATIONS

Lee, Won-Yong, Tris (2,2'-bipyridyl)ruthenium(II) Electrogenerated Chemiluminescence in Analytical Science, Mikrochimica Acta, 1997, pp. 19-39, vol. 127.
Wang, Jie et al., Development and Application of Pipeline Electrochemical Immunoassay Analyzer, 13th National Conference on Sensitive Components and Sensors, 2016, pp. 917-923, vol. 10, No. 27.
Zhou, Dan, Introduction to Emergency Medical Equipment Engineering, People's Military Medical Publishing House, 2006, p. 243.
Sun, "Application of Surfactants in Analytical Chemistry and the Environment", 2006, p. 74.

* cited by examiner

| | detection | problem | occasional occurrence | systematic occurrence |
|---|---|---|---|---|
| 1 | gas bubble between sample and co reactant | too early, sample volume too low | flagging of result +warning | alarm, interruption of measurement |
| 2 | gas bubble between sample and co reactant | too late, co reactant volume flow too low | flagging of result +warning | alarm, interruption of measurement possibile malfunction: dilutor seal faulty, valve faulty |
| 3 | gas bubble between co reactant and cleaning solution | too late, cleaning solution volume flow too low | flagging of result +warning | alarm, interruption of measurement possibile malfunction: dilutor seal faulty, valve faulty |
| 4 | gas bubble of cleaning | too late, cleaning solution volume flow too low | flagging of result +warning | alarm, interruption of measurement possibile malfunction: dilutor seal faulty, valve faulty |
| 5 | gas bubble between cleaning solution and co reactant | too late, co reactant solution volume flow too low | flagging of result +warning | alarm, interruption of measurement possibile malfunction: dilutor seal faulty, valve faulty |
| 6 | gas bubble in between co reactant and sample | gas bubble detected even though no gas bubble was expected | flagging of result +warning | alarm, interruption of measurement possibile malfunction: valve faulty |

Fig. 9

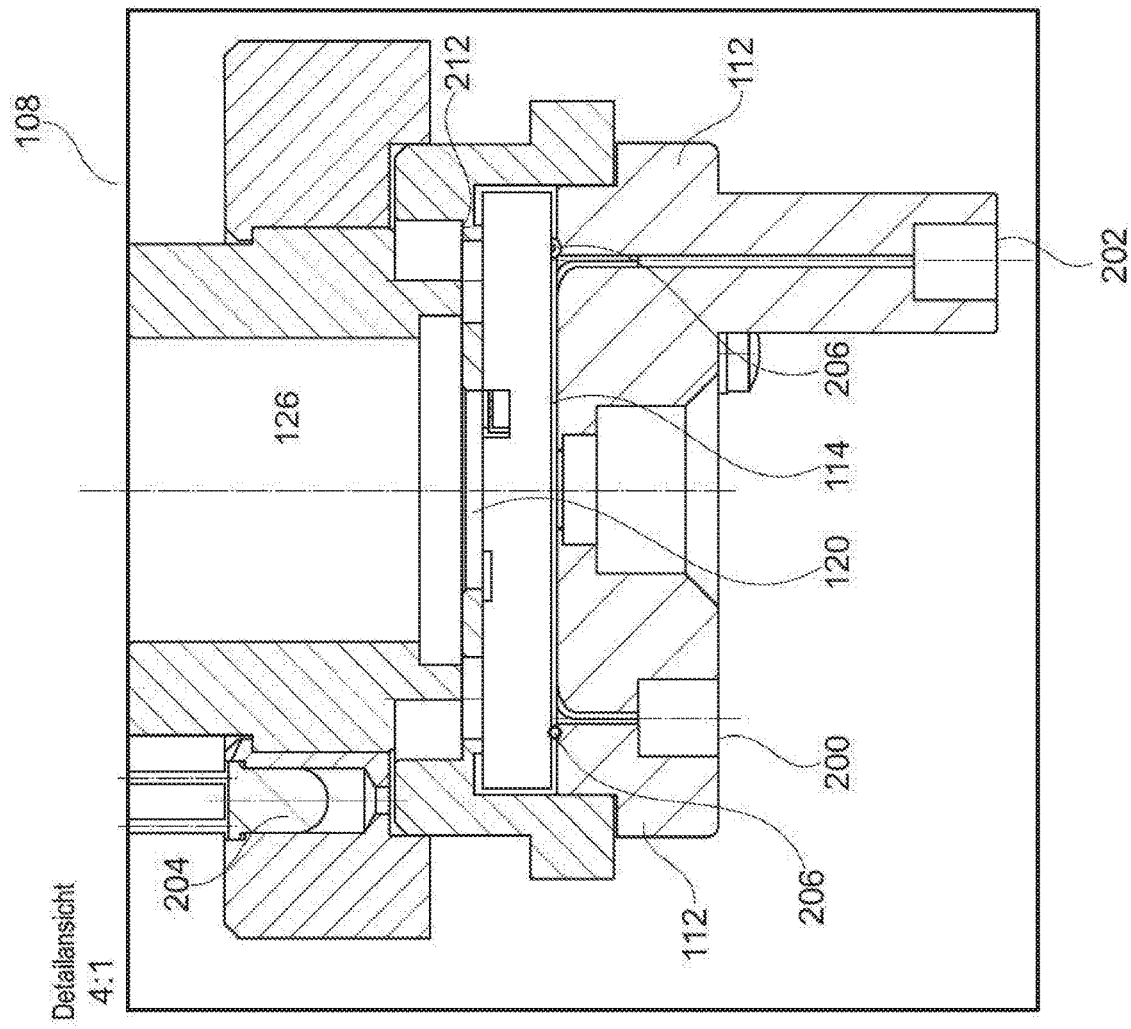
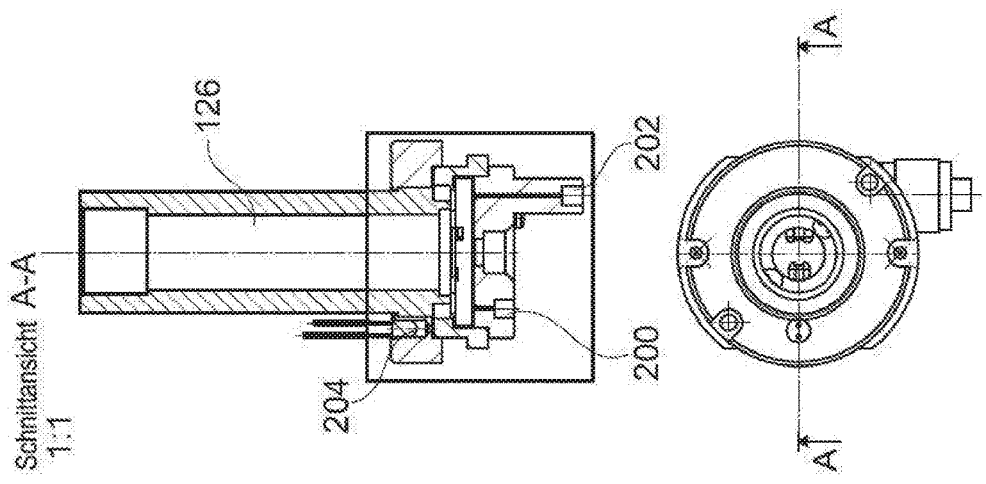
Fig. 10

METHOD OF MONITORING AN OPERATION OF DETECTION OF AN ANALYTE IN A LIQUID SAMPLE

CROSS-REFERENCE TO RELATED APPLICATIONS

This application is a continuation of International Patent Application No. PCT/EP2018/069937, filed 23 Jul. 2018, which claims the benefit of European Patent Application No. 17184342.8, filed 1 Aug. 2017, the disclosures of which are hereby incorporated herein by reference in their entirety.

TECHNICAL FIELD

The present disclosure relates to a method of monitoring an operation of detection of an analyte in a liquid sample using a measurement cell, as well as an apparatus for monitoring an operation of detection of an analyte in a liquid sample using a measuring cell and a computer program product.

BACKGROUND

Electrochemiluminescent (ECL) assay techniques are well known for the detection and quantitation of analytes of interest in biochemical and biological substances. Generally, methods and systems which are capable of measuring trace amounts of microorganisms, pharmaceuticals, hormones, viruses, antibodies, nucleic acids and other proteins are of great value to researchers and clinicians.

ECL assay techniques provide a sensitive and precise measurement of the presence and concentration of an analyte of interest. In such techniques, the incubated sample is exposed to a potentiostatically or galvanostatically controlled working electrode in order to trigger luminescence. In the proper chemical environment, such electrochemiluminescence is triggered by a voltage or current impressed on the working electrode at a particular time and in a particular manner. The light produced by the label is measured and indicates the presence or quantity of the analyte. For a fuller description of such ECL techniques, reference is made to, e.g., U.S. Pat. No. 5,238,808, and WO 86/02734.

An electrochemiluminescence method of detecting an analyte in a liquid sample, where specific protein (e.g., streptavidin or Biotin) coated magnetic microparticles are stirred within a receptacle to prevent them from deposition at the bottom and aggregation with each other, is described in WO 2014/202298 A1 together with a suitable analysis system. WO 90/11511 discloses a method and an apparatus for conducting electrochemiluminescent measurements using a voltage waveform with a decreasing scan rate applied at a voltammetric working electrode to improve the precision and accuracy of measurements. In WO 99/39206, a method for analyzing a test sample by means of an electro-chemiluminsecence bond reaction test is described, wherein a complex containing a chemoluminescence marker, which is characteristic for the analysis, is formed through a biochemical bond reaction and bonded to a magnetic microparticle during a reaction sequence. In "Tris (2,2'-bipyridyl)ruthenium(II) Electrogenerated Chemiluminescence in Analytical Science", Microchim. Acta 127, 19-39, W.-Y. Lee describes how tris (2,2'-bipyridyl)ruthenium(II) electrogenerated chemiluminescence can be used as a detection method for the determination of oxalate and a variety of amine-containing analytes without derivatization in flowing streams such as flow injection and H PLC.

U.S. Pat. No. 6,599,473 B1 discloses an electrochemiluminescence binding reaction analysis (ECL-BRA).

In accordance with ECL-BRA a detectable complex is produced, whose concentration constitutes a measure of the analytic result sought. A marking substance (label) capable of effecting an ECL-reaction is coupled to a binding reagent specific for the analyte, e.g., an antibody. The species comprising the marking substance and the binding reagent is designated as a label conjugate.

When such a substance is subjected to a suitable electrical potential on a voltammetric working electrode, it emits light which can be measured photometrically. A second electrochemically active substance, designated as a co-reactant, normally contributes to this reaction. In practice, primarily a ruthenium complex (ruthenium-tris [bipyridyl]) is used as ECL-label in combination with tripropylamine (TPA) as co-reactant. The two electrochemically active substances are both oxidized upon voltage application to the electrode. Subsequent loss of a proton will turn the TPA into a strongly reducing species. The subsequent redox reaction brings the ECL-label into an excited state from which it returns to the ground state with the emission of a photon. The ECL-label reaction is typically a circular reaction so that a single label molecule emits a plurality of photons after application of a voltage to the electrode.

The ECL-marked complex molecules characteristic for the analysis are fixed to magnetic microparticles (beads). In practice, magnetized polystyrene beads having a diameter of typically 2 to 3 micrometers are used. Fixing is effected by means of a pair of specific biochemical binding partners. The pair streptavidin biotin has turned out to be particularly advantageous. The beads are streptavidine-coated, to which a biotinylated antibody will bind.

The beads with the bound marked complex are introduced into the measuring cell of a measuring apparatus. The cell is equipped with electrodes which are necessary for generating the electrical field required for triggering the ECL-reaction. The beads are drawn onto the surface of the working electrode in the magnetic field of a magnet disposed below the working electrode. Since this typically occurs in flow-through cells with continuously flowing sample fluids, the magnetic deposition of the beads is designated as "capturing". An electric potential required for triggering the ECL-reaction is then applied to the working electrode and the resulting luminescence light is measured using a suitable optical detector. The intensity of the luminescence light is a measure for the concentration or the number of labeled antibodies coupled to the beads on the surface of the working electrode which, in turn, is a measure of the concentration of the analyte in the sample. A calibration allows calculation of the sought concentration from the measured luminescence signal.

U.S. Patent Application Publication No. 2001/0008612 A1 discloses an apparatus for the conduct of electrochemiluminescence measurements which includes an ECL chamber having a transparent window defining one wall of the chamber and a photodetector mounted closely adjacent thereto. An assay fluid is subject to a magnetic field and is electrically energized. Electrochemiluminescence induced in the fluid is measured by the photodetector.

U.S. Patent Application Publication No. 2006/0042963 A1 discloses a method for detecting the presence or absence of a gas bubble in an aqueous liquid, comprising providing an amperometric sensor positioned within a measuring chamber, wherein the amperometric sensor is configured to determine the concentration of a gaseous component dissolved in a liquid.

U.S. Pat. No. 5,583,635 relates to a method of measuring particles and an apparatus for the same, which count only particles in liquid by distinguishing between the particles and bubbles in liquid.

BRIEF SUMMARY

It is against the above background that the embodiments of the present disclosure provide certain unobvious advantages and advancements over the prior art. In particular, the inventors have recognized a need for improvements in a method and an apparatus for monitoring an operation of detection of an analyte in a liquid sample.

In accordance with an embodiment of the present disclosure, a method of monitoring an operation of detection of an analyte in a liquid sample using a measuring cell is provided, the measuring cell comprising a working electrode for excitation of electrochemiluminescence in the liquid sample, an optical detector for detecting the excited electrochemiluminescence for, e.g., determining the analyte from the detected electrochemiluminescence, the excitation and detection being performed in an electrochemiluminescence measurement cycle, the measurement cycle comprising transporting the liquid sample via a transport path to the working electrode using a support liquid, the method comprising:
- coupling light of a light source into the transport path during part of the measurement cycle, the transport path forming a light guide between the light source and the optical detector,
- detecting the coupled light by the optical detector,
- analyzing the detected light regarding the presence of a gas bubble in the transport path,
- providing a measurement state in case the result of the analysis deviates from a target state regarding the presence of a gas bubble in the transport path.

In accordance with another embodiment of the present disclosure, an apparatus for monitoring an operation of detection of an analyte in a liquid sample using a measuring cell is provided, the apparatus comprising the measuring cell, the measuring cell comprising a working electrode for excitation of electrochemiluminescence in the liquid sample and an optical detector for detecting the excited electrochemiluminescence and a processing unit for determining the analyte from the detected electrochemiluminescence, the apparatus being adapted for performing the excitation and detection in an electrochemiluminescence measurement cycle, the measurement cycle comprising transporting the liquid sample via a transport path to the working electrode using a support liquid, the apparatus comprising a processor and a memory, the memory comprising computer executable instructions, execution of the instructions by the processor causing the apparatus to:
- coupling light of a light source into the transport path during part of the measurement cycle, the transport path forming a light guide between the light source and the optical detector,
- detecting the coupled light by the optical detector,
- analyzing the detected light regarding the presence of a gas bubble in the transport path,
- providing a measurement state in case the result of the analysis deviates from a target state regarding the presence of a gas bubble in the transport path.

BRIEF DESCRIPTION OF THE DRAWINGS

The following detailed description of the embodiments of the present disclosure can be best understood when read in conjunction with the following drawings, where like structure is indicated with like reference numerals and in which:

FIG. 5 shows PMT measurement results over the measurement cycle when the light source is permanently turned on;

FIG. 9 is a decision table, according to which a measurement state can be provided; and FIG. 10 illustrates various cross sections through a measurement cell.

Figure 1:
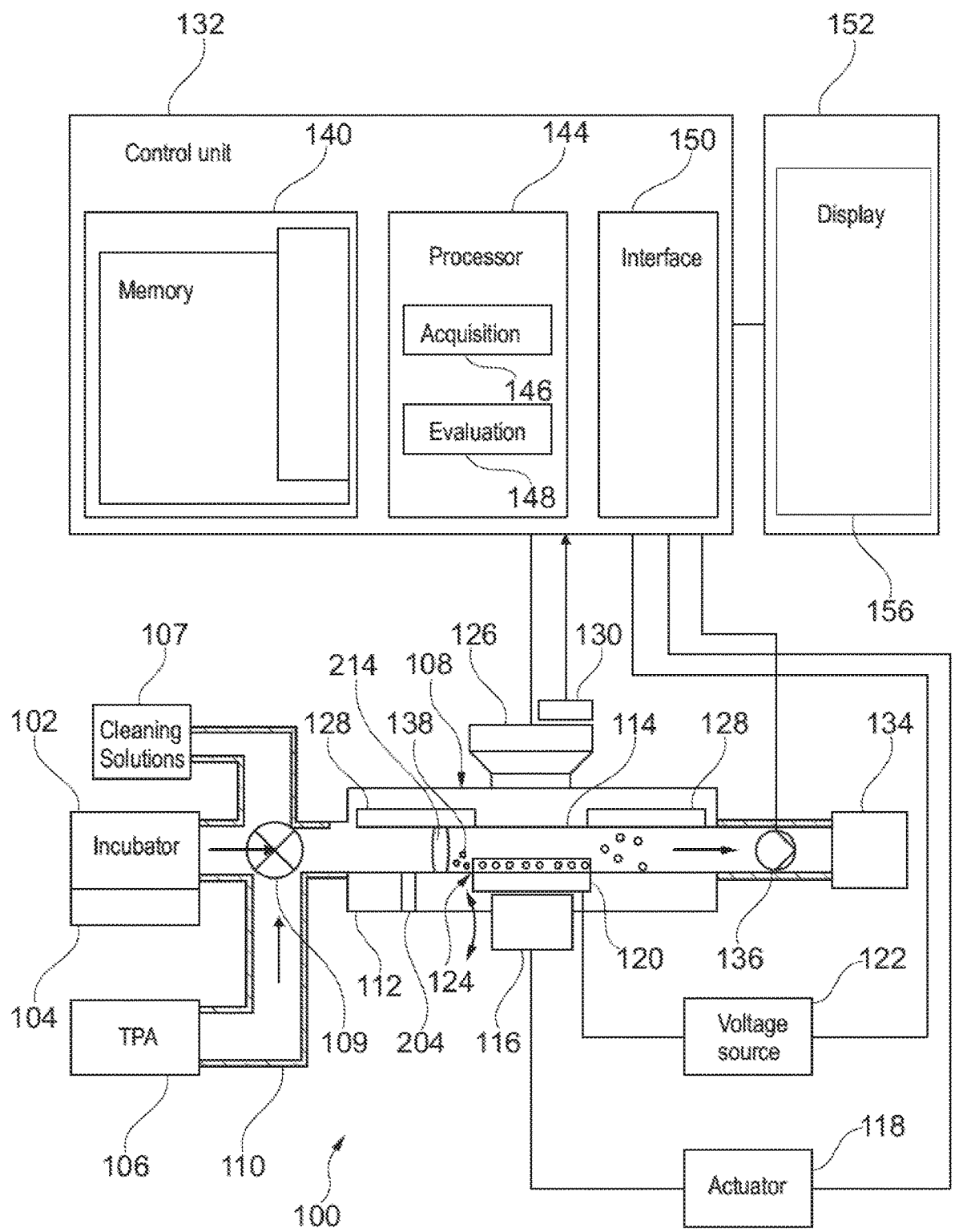
FIG. 1 is a block diagram of an analysis system.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

An 'analyte' as understood herein is a component of the liquid sample to be analyzed, e.g., molecules of various sizes, proteins, metabolites and the like.

A 'liquid sample' as understood herein encompasses a biological sample such as any kind of tissue or body fluid having been derived from a human or any other organism. In particular, a biological sample can be a blood-, serum-, plasma-, urine-, cerebral-spinal fluid-, or saliva-sample or any derivatives thereof.

A 'measurement cycle' as understood herein encompasses the individual steps that are required in order to perform the electrochemiluminescence detection of the analyte in the liquid sample.

An optical detector may be any device that is capable to detect light. Examples are photomultipliers, phototubes, microchannel plate detectors, semiconductor active-pixel sensors, cadmium zinc telluride detectors, etc.

For example, the electrochemiluminescence is excited for the purpose of determining the analyte from that detected electrochemiluminescence.

A light source may be any source that provides light for coupling into the transport path in a controllable manner. Controllable manner means that the duration and/or intensity of the light can be fully controlled.

Embodiments of the disclosure may have the benefit that on one hand gas bubbles in the transport path can be used in order to increase the quality of determining an analyte from the detected electrochemiluminescence. The gas bubbles can be intentionally and controllably channelled into the transport path for example to separate different kinds of liquids transported in the transport path from each other in order to avoid an unintentional mixture of the liquids. Further, the gas bubbles may also be intentionally channelled into the transport path for inducing a mechanical interaction between the air-liquid interface of the air bubbles and the surrounding liquid with the working electrode. This can be performed for example for enhancement of cleaning purposes of the working electrode.

Since the described method is capable of providing a measurement state in case the result of the analysis of the detected light regarding the presence of a gas bubble deviates from a target state regarding the presence of a gas bubble in the transport path, it may be possible to detect anomalies regarding gas bubbles in the transport path. These anomalies may include gas bubbles at time points or locations of the transport path where for example no gas bubbles are expected or desired. It may also provide the possibility to detect anomalies of gas bubbles that on one hand side are desired at a certain time point in the measurement cycle, however only with rather specific properties (for example the size of the gas bubble or the exact time point at which in the measurement cycle the presence of the gas bubble is expected).

In accordance with an embodiment of the disclosure, the gas bubble is separating the liquid sample and the support liquid. However, it is also possible that a gas bubble can be detected using the above mentioned method which separates two different support liquids in the transport path.

In accordance with an embodiment of the disclosure, in case of the presence of the gas bubble the method further comprises analyzing the detected light regarding a property of the gas bubble, the measurement state indicating a deviation of the property from a reference property by a predefined threshold. For example, the property is selected from any one of: a time duration for which the gas bubble is detected, a time point at which the gas bubble is detected, an intensity of the detected coupled light.

For example, in case no gas bubble is expected at all at a certain time point, the target state that is expected at said time point is 'no gas bubble'. In case there is any gas bubble independent of the size of the gas bubble detected at said time point, the measurement state will be an error or a flag or some other kind of information that is provided and that indicates some malfunction in the system. On the other hand, in case a gas bubble is detected at a certain time point, a property of the gas bubble 'time duration for which the gas bubble is detected' may be measured and compared with a predefined threshold. The predefined threshold may define a minimum and maximum time duration for which the gas bubble is detected. In case the measured time duration is outside the range of time duration defined by the predefined threshold, again the measurement state may be an error, the indication of information of a malfunction of the system, etc.

It has to be noted here that the time duration for which the gas bubble is detected could be used as a direct indication for the size of the air bubble. Since the transport velocity of the liquid in the transport path is known, the velocity of the gas bubble in the transport path is evident. Therefore, from the time duration for which the gas bubble is detected directly the length of the gas bubble can be deduced. Under the assumption that the gas bubble completely fills the cross-section of the transport path, the total volume of the gas bubble can be calculated. Similarly, in case a liquid is 'sandwiched' between two gas bubbles, from the time points of detection of the gas bubbles and the transport velocity of the liquid in the transport path the exact volume of the sandwiched liquid may be determined.

In a further example, the intensity of the detected coupled light might be a direct indication of the volume of the gas bubble. Either a dedicated formula may be used which directly links the detected light intensity of the coupled light to a certain volume of the gas bubble or a lookup table may be used from which depending on the intensity of the coupled light the respective volume of the gas bubble can be deduced.

In accordance with an embodiment of the disclosure, the intensity of the detected coupled light is associated with a volume of the gas bubble, the reference property corresponding to a minimum volume of the gas bubble, the liquid sample and the support liquid being provided to the transport path through a pipe, the working electrode being contained in a measurement chamber being part of the transport path, the minimum volume of the gas bubble being selected such that at any location within the transport path and the pipe the gas bubble completely fills the cross section at this location of the transport path and the pipe, the cross section being perpendicular to the direction of transport of the liquid sample or the support liquid at this location.

For example, the measurement cycle comprises sucking a gas into the transport path for forming the gas bubble in the transport path. For example, the gas bubble is separating the liquid sample and the support liquid.

By ensuring that the requirements regarding the minimum volume of the gas bubble is met, the quality of separation between two liquids may be guaranteed. The gas bubble therefore mechanically separates the two liquids that are directly adjoining the gas bubble such that any kind of mixing of these two liquids is prevented. Especially a movement of the gas bubble at least partially through different liquids due to a too large inner diameter of the transport path compared to the diameter of the gas bubble may be prevented.

In accordance with an embodiment of the disclosure, the transport path is completely located within the measuring cell, the light source coupling the light into the transport path through a wall geometrically limiting the size of the transport path. This may have multiple advantages: first of all by means of integrating the transport path and the light source completely into the measuring cell a well and predefined environment is provided in which measurements of the intensity of the coupled light can be performed in a controlled and reproducible manner. Instead of using for example a transparent pipe into which the light is coupled and which can be plugged into the measuring cell for providing the respective fluids to the transport path, by directly coupling the light into the transport path through a wall geometrically limiting the size of the transport path any mechanical transitions between such a pipe and the measuring cell are avoided. Any such transition will be subject to a slight deviation of the detected coupled light in case the light is coupled into the pipe itself and would depend on the way the pipe is attached to the measuring cell. Bigger or smaller gaps between the pipe and the measuring cell will result in different results in intensity of the detected coupled light.

Further, avoiding any mechanical altering of the flow path used for transporting the liquid sample to the measuring cell by gaps between the pipe and the measuring cell will provide for a laminar and turbulence free flow of the liquid sample. This in turn enhances the reproducibility of the ECL measurements since they will always be performed for liquids that were provided to the measuring cell under the same flow conditions.

A further advantage of this embodiment may be that the optical detector that is used for detecting the excited electrochemiluminescence can also be used for detecting the coupled light at a rather high reliability and efficiency: the coupled light arrives from the 'integrated light source' in a very well defined manner at the optical detector, independent of any mechanical transitions between a pipe and the measuring cell. Thus, a one-time calibration of the optical detector and the light source is sufficient for obtaining reliable measurement states from the light analysis.

For example, the measuring cell is comprising an integrated inlet port and an integrated outlet port, the working electrode being contained in a measurement chamber, the measurement chamber being in first fluid connection with the inlet port and the outlet port, the first fluid connection and the measurement chamber forming the transport path, the inlet port being adapted for receiving a pluggable pipe (for example the one as discussed above) in second fluid connection with a reservoir containing the liquid sample. The inlet port may also be adapted for receiving the pluggable pipe in second fluid connection with a reservoir containing the support liquid. A valve may be used to switch between the liquid sample and the support liquid. Alternatively, only a single second fluid connection may be used which may be dipped at one time point into a reservoir comprising the liquid sample and at another time point in a reservoir containing the support liquid. In case the second fluid connection is within a gas reservoir, for example the ambient environment, a gas like for example air may be sucked into the pluggable pipe.

The pluggable pipe has only the purpose of providing the respective fluids to the transport path, whereas only the transport path is used for conducting the coupled light from the light source to the optical detector.

The optical detector is used for both, detecting the excited electrochemiluminescence, as well as detecting the coupled light.

In accordance with an embodiment of the disclosure, the light source is integrated in the measuring cell.

In accordance with an embodiment of the disclosure, the light source is turned off during the detection of the excited electrochemiluminescence. This way it may be ensured that the electrochemiluminescence detection and therefore the determination of the analyte from the detected electrochemiluminescence is not disturbed by the light of the light source.

In accordance with an embodiment of the disclosure, the providing of the measurement state comprises displaying the measurement state on a display coupled to the measuring cell. As mentioned above, a measurement state may indicate a malfunction of the system, a dedicated flagging of the determined analyte from the detected electrochemiluminescence, as well as a possibility for providing recommendations to a user of the system for resolving an eventual problem that was identified regarding the analyte detected light.

In accordance with an embodiment of the disclosure, in case the measurement state is provided in accordance with a predefined repetition pattern for multiple ones of the liquid sample, the method further comprises stopping the operation of the measurement cell. For example, in case the measurement state is provided in a systematic manner for every liquid sample or for every second liquid sample or in case for one single liquid sample within a single measuring cycle multiple measurement states are provided, this may be indication of a malfunction of parts of the measuring cell or the components that are used in order to provide the respective fluids to the measuring cell.

In accordance with an embodiment of the disclosure, the measurement cycle can comprise any one of the following:
a first phase for conditioning of the working electrode without the liquid sample using an auxiliary solution as the support liquid, the first phase comprising taking up the auxiliary solution as the support liquid into the transport path,
a second phase for the transporting of the liquid sample to the working electrode and capturing of magnetic microparticles, said liquid sample comprising a marking substance capable of effecting an electrochemiluminescence reaction to be detected as the electrochemiluminescence excitation, said complex further being bound to the magnetic microparticles, said capturing comprising attracting the microparticles by a magnetic field thereby depositing the microparticles on a surface of said working electrode, the second phase comprising taking up the liquid sample into the transport path and transporting the liquid sample to the working electrode by subsequently taking up the auxiliary solution as the support liquid into the transport path,
a third phase for washing of the working electrode after the capturing and before the excitation of the electrochemiluminescence, said third phase being adapted to remove unbound complexes from the working electrode, the washing being performed using the auxiliary solution as the support liquid, the third phase comprising taking up the auxiliary solution as the support liquid into the transport path,
a fourth phase for performing the electrochemiluminescence measurement on the sample,
a fifth phase for cleaning of the working electrode with a cleaning solution, the fifth phase comprising taking up the cleaning solution into the transport path,
the target state regarding the presence of a gas bubble separating the liquid sample and the support liquid being any one of the following:
no gas bubble in between the support liquid and the liquid sample when switching from the first phase to the second phase,
a gas bubble in between the support liquid and the liquid sample when switching from the second phase to the third phase,
a gas bubble in between the support liquid and the cleaning solution when switching from the fourth phase to the fifth phase,
a gas bubble in between the cleaning solution and the support liquid when switching from the fifth phase to the first phase for a subsequent run of the measurement cycle.

For example, the auxiliary solution may be a co-reactant solution. Herein, the term 'co-reactant solution' (=CoS) is to be considered as a synonym for the reagent required as the ECL co-reactant. For example, 'co-reactant solution' may comprise Tripropylamine (TPA). A composition suitable as co-reactant solution (CoS) comprises for example 180 mM TPA, 300 mM Phosphate, 0.1% detergent (e.g., polidocanol), pH of 6.8.

Further, the term 'cleaning solution' is to be considered as a synonym for a measuring cell cleaning solution that is used to clean the cell after having performed the ECL measurement. For example, 'cleaning solution' may comprise Potassium Hydroxide. A composition suitable as cleaning solution comprises for example 176 mM KOH and 1% detergent (e.g., polidocanol).

For example, no gas bubble may be desired in between the support liquid and the liquid sample when switching from the first phase to the second phase since in this case the electrochemiluminescence measurements do not provide reproducible and therefore reliable measurement results. On the other hand, a gas bubble may be required in between the support liquid in the liquid sample when switching from the second phase to the third phase since after capturing of the magnetic microparticles of the liquid sample it is desired that any subsequent liquid flowing over the working electrode does not contain any microparticles anymore, since this would also alter the electrochemiluminescence measurement results. The optional gas bubble between the support liquid and the cleaning solution when switching from the fourth phase to the fifth phase and also the optional gas bubble in between the cleaning solution and the support solution when switching from the fifth phase back to the first phase for the next and subsequent run of the measurement cycle may ensure, that the cleaning capabilities of the cleaning solution and the working electrode conditioning capabilities of the support liquid are not diminished due to an unwanted mixing of the support liquid and the cleaning solution.

It may also be beneficial to use multiple air bubbles during the fifth phase of cleaning the working electrode with the cleaning solution. In other words, the cleaning solution contains multiple ones of the gas bubbles which mechanically supports the cleaning of the working electrode by 'pulling away' remaining magnetic particles from the working electrode.

In accordance with an embodiment of the disclosure, the gas can comprise any one of the following: air, inert gas, nitrogen.

In accordance with an embodiment of the disclosure, the transporting of the liquid sample via the transport path to the working electrode using the support liquid is performed using a suction device adapted for sucking the liquid sample and the support liquid into the transport path. For example, as a suction device a pump may be used which is located behind the measuring cell and that aspirates liquids through the transport path from one or more respective reservoirs to which the transport path is connected via a respective pipe. For example, the transporting of the liquid sample via the transport path may be performed at a velocity within a range of about 5 to about 1000 µl per second, typically within a range of about 20 to about 400 µl per second. Also, in an example the volume of the gas bubble may be within the range of about 5 to about 100 µl, typically within the range of about 10 to about 30 µl.

It has to be noted that the above described method may also be used to determine the volume of one or more of the liquids that are used for performing the electrochemiluminescence measurement. In case between the first and the second phase no gas bubble was detected, the time point at which the gas bubble is detected in between the support liquid and the liquid sample when switching from the second phase to the third phase is representative of the volume of the liquid sample that was taken into the transport path. For example, in case the reservoir that contained the liquid sample did not contain a sufficient volume of liquid sample, instead of liquid sample consequently air would have been sucked from said reservoir into the transport path. The sudden presence of that air in the transport path may be detected using the above described method and it can be deduced, that the liquid sample volume was not satisfying a predefined volume that was expected and even the volume aspirated from the reservoir can be calculated therefrom.

In accordance with another embodiment of the disclosure, an apparatus for monitoring an operation of detection of an analyte in a liquid sample using a measuring cell is provided, the apparatus comprising the measuring cell, the measuring cell comprising a working electrode for excitation of electrochemiluminescence in the liquid sample and an optical detector for detecting the excited electrochemiluminescence and a processing unit for determining the analyte from the detected electrochemiluminescence, the apparatus being adapted for performing the excitation and detection in an electrochemiluminescence measurement cycle, the measurement cycle comprising transporting the liquid sample via a transport path to the working electrode using a support liquid, the apparatus comprising a processor and a memory, the memory comprising computer executable instructions, execution of the instructions by the processor causing the apparatus to:

coupling light of a light source into the transport path during part of the measurement cycle, the transport path forming a light guide between the light source and the optical detector, detecting the coupled light by the optical detector, analyzing the detected light regarding the presence of a gas bubble in the transport path, providing a measurement state in case the result of the analysis deviates from a target state regarding the presence of a gas bubble in the transport path.

Described is also a measuring cell for monitoring an operation of detection of an analyte in a liquid sample, the measuring cell comprising a working electrode for excitation of electrochemiluminescence in the liquid sample and an optical detector for detecting the excited electrochemiluminescence, the measuring cell being adapted for performing the excitation and detection in an electrochemiluminescence measurement cycle, the measurement cycle comprising transporting the liquid sample via a transport path to the working electrode using a support liquid, the measuring cell comprising:

a light source adapted for coupling light into the transport path during part of the measurement cycle, the transport path forming a light guide between the light source and the optical detector.

In another aspect the disclosure relates computer program product comprising computer executable instructions to perform the method as described above.

In order that the embodiments of the present disclosure may be more readily understood, reference is made to the following examples, which are intended to illustrate the disclosure, but not limit the scope thereof.

FIG. 1 shows an analysis system 100 for detecting an analyte in a liquid sample. The analysis system is also designated as the 'measurement apparatus'. The analysis system 100 comprises an incubator 102 for receiving a liquid 104 that is a mixture of an aliquot of the liquid sample "incubate" and a marker for marking the analyte, such as of a luminescence immunoassay.

The analysis system 100 comprises a reservoir 106 that contains the co-reactant of the electrochemical reaction causing the luminescence. The incubator 102 and the reservoir 106 are coupled to a measuring cell 108 of the analysis system by a pipe system 110 through which a portion of the liquid 104 and the co-reactant can flow into the measuring cell 108.

FIG. 10 illustrates various cross sections through the measurement cell 108. As can be seen from both, FIG. 1 and FIG. 10, the measuring cell 108 comprises a cell body 112 that has a conduit 114 "transport path" for receiving a portion of the liquid 104 and of the co-reactant through the pipe system 110. The pipe system 110 may be connected to an inlet port 200 of the measuring cell 108. An outlet port 202 of the measuring cell 108 may be in fluid connection to a liquid waste container 134.

The measuring cell 108 has a magnetic component 116, such as a permanent magnet, for providing a magnetic field in the measuring cell. The magnetic component 116 may be coupled to an actuator 118 for rotating the magnetic component 116 to and from the conduit 114 in order to switch on or off the magnetic field within the conduit.

The magnetic component 116 is positioned below a working electrode 120 that is coupled to a voltage source 122. An excitation area 124 is formed in the conduit 114 within the magnetic field caused by the magnetic component 116 on the working electrode 120.

Luminescence that is caused in the excitation area 124 by the application of excitation energy, i.e., the application of a voltaic pulse on the working electrode 120, is measured by means of an optical sensor, such as a photomultiplier tube PMT 126.

The photomultiplier 126 is positioned opposite to the excitation area 124 over a window formed by counter electrodes 128 of the working electrode 120 through which the luminescence photons and by the excitation energy impinge on the photomultiplier 126.

A resultant time resolved measurement signal 130 is provided from the photomultiplier 126 to a control unit 132 of the analysis system 100.

The transport path is confined towards the PMT 126 by a transparent window 212 and seals 206 between the window and the cell body 112.

After a measurement has been performed the liquid contained within the conduit 114 is removed into the liquid waste container 134 and the measuring cell 108 is regenerated for a subsequent acquisition of a measurement signal.

The control unit 132 is coupled to the voltage source 122 in order to control the voltage source 122 to apply the signal to the working electrode 120. The control unit 132 is also coupled to the actuator 118 for controlling the actuator 118 to switch on and off the magnetic field by moving the permanent magnet correspondingly.

Further, the control unit 132 may be coupled to a 'sipper unit', i.e., a pump 136, for extracting a portion of the liquid 104 from the incubator 102 and a portion of the co-reactant from the reservoir 106 as well as for removing the liquid from the measuring cell 108 and regeneration of the measuring cell. In addition the control unit 132 may be coupled to additional robotic components such as a pipetting station.

The measuring cell 108 may be adapted for performing ECL-BRA using various luminescence immunoassays.

Even though ECL-BRA is discussed in the following, this is only an example and this example may be extended by the skilled person to other ECL techniques.

For example, the liquid 104 may contain a mixture of an aliquot of the liquid sample, streptavidin coated magnetic particles, biotinylated antibodies and ruthenylated antibodies to form a so-called 'sandwich' whereas the co-reactant contained in the reservoir 106 is tripropylamine (TPA). Hence, magnetic particles 138 with a bound label flow into the conduit 114. The magnetic particles 138 are immobilized on the working electrode 120 when the magnetic field is switched on. Next, the pulse is applied on the working electrode 120 to cause the electrochemiluminescence in accordance with the ECL-BRA technique.

The control unit 132 has an electronic memory 140 for storing reference data that describes the luminescence decay of a valid measurement signal without a superimposed interfering signal. That reference data is specific for the luminescence immunoassay that is utilized for the detection of the analyte.

In the embodiment considered here the reference data is stored in a lookup table or database table. The reference data comprises a reference dataset for each luminescence immunoassay supported by the analysis system 100. For example, for each supported immunoassay two coefficients a and b as well as a time t is stored in the memory. The coefficients a and b describe a linear law relating the maximum amplitude of the luminescence signal to a luminescence level reached after the decay time t. Storing the decay time t as part of the reference data may be superfluous if the considered decay time t is always the same.

The control unit 132 has at least one electronic processor 144 for execution of program modules contained in the memory 140. For example a program module 146 is executed by the processor 144 for acquisition of an ECL measurement signal. Another program module 148 is executed by the processor 144 for evaluation of the acquired measurement signal.

Further shown in FIGS. 1 and 10 is a light source 204, for example an LED. The light source is arranged in the measuring cell 108 and adapted to couple light into the transport path 114. The transport path 114 and any liquid contained in the transport path are forming a light guide between the light source and the PMT 126. The PMT 126 can detect the coupled light. By executing further instructions contained in the memory 140, the processor 144 can analyze the detected light regarding the presence of a gas bubble 214 in the transport path and provide a measurement state in case the result of the analysis deviates from a target state regarding the presence of a gas bubble in the transport path 114. The presence of a gas bubble in the transport path 114 leads to a change of the optical refraction properties and the optical light scattering properties of the liquid contained in the transport path. Therefore, the instructions contained in the memory 140 can derive from the detected light if first at all a gas bubble is present at all in the transport path and second a physical property of the gas bubble like, e.g., the volume of the gas bubble.

The control unit 132 has an interface 150 for coupling a display unit (or display) 152 or another human-machine-interface to the control unit 132. The interface 150 may be implemented as a graphical user interface for displaying a window 156 for displaying a result of the analysis of the detected light. For example, a measurement state can be displayed in case the result of the analysis of the detected light deviates from a target state regarding the presence of a gas bubble in the transport path.

Figure 2:
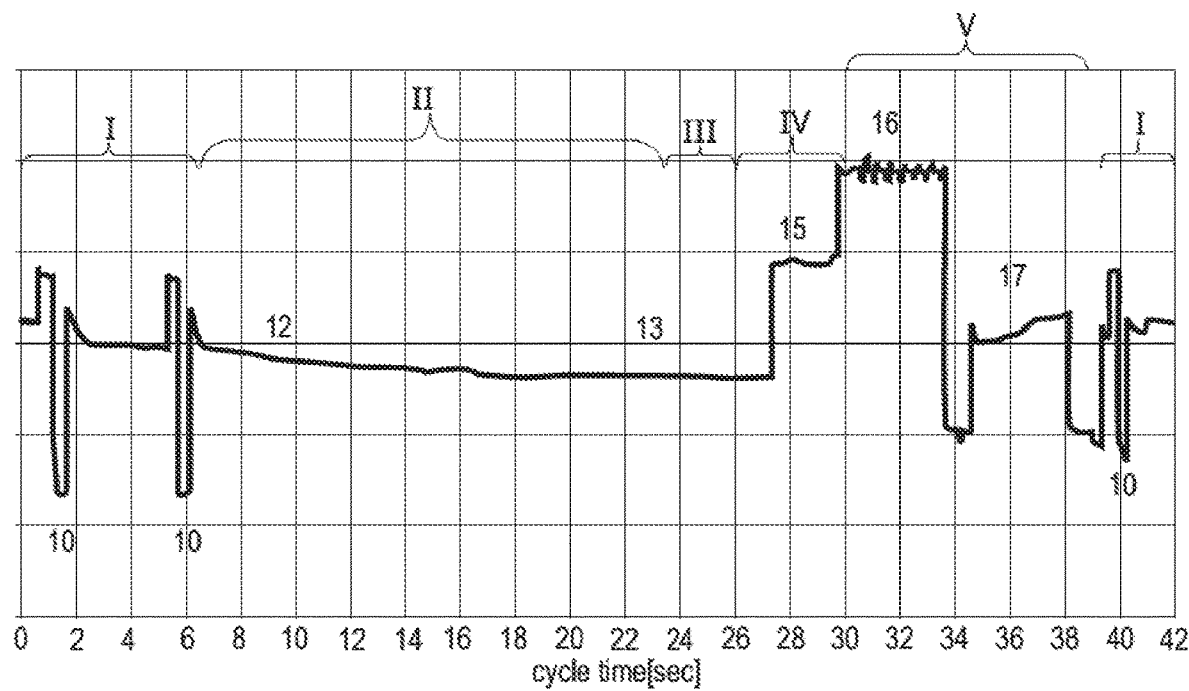
FIG. 2 is a timing diagram represented by the voltage measured at the working electrode.
Figure 3:
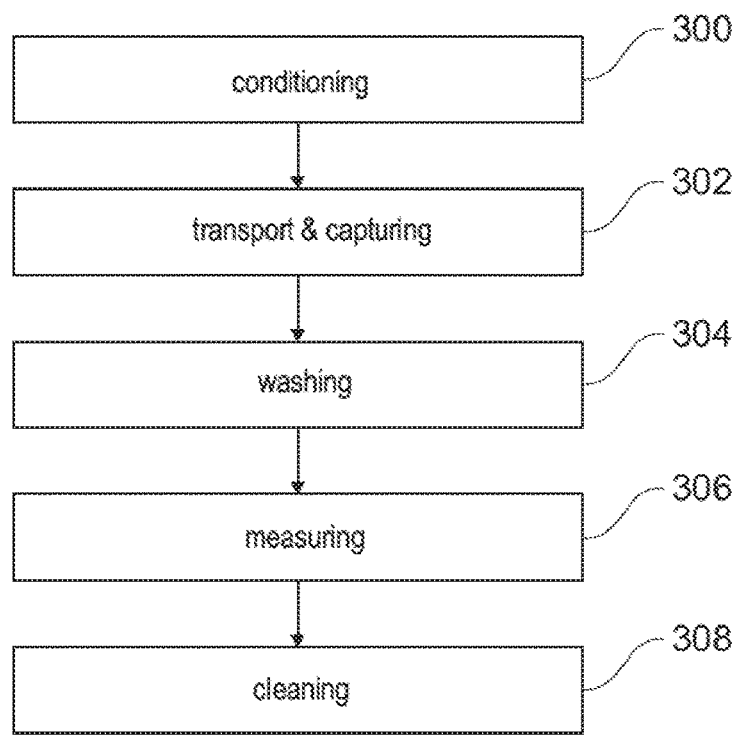
FIG. 3 is a flow chart describing the ECL-BRA technique.

In the following, the ECL-BRA technique will be described in combination with FIGS. 1, 2 and 3. FIG. 2 is a timing diagram represented by the voltage measured at working electrode and showing the different phases of ECL-BRA, and FIG. 3 is a respective flow chart.

The method starts in block 300 (phase i) which is a conditioning phase in which a DC potential is applied with certain voltage profile 10. The solid line in FIG. 2 is the potential profile applied at the working electrode 120 with respect to the counter electrode 128. The conditioning has the purpose of preparing the working electrode for the subsequent measurements—conditioning is used to insure that the electrode has a known surface state at the start of the subsequent measurements. The conditioning is performed using the support liquid 'co-reactant solution' CoS.

In operation a user selects one of the luminescence immunoassays supported by the analysis system 100 by entering a respective selection into the window 156. The analysis of the liquid sample is started by execution of the program module 146 such that the pump 136 is controlled to transport a portion of the liquid sample 104 and of the co-reactant into the conduit 114.

Next, the actuator 118 is controlled to flip the permanent magnet into a position such that its magnetic field is applied to the conduit 114 for immobilization, i.e., capturing of the magnetic particles with their bound labels on the working electrode 120. The process of transport of the liquid sample 104 and capturing of the magnetic particles is designated with block 302 and corresponds to phase ii in FIG. 2.

When switching from phase i. to phase ii., i.e., switching from aspiration of CoS to aspiration of the liquid sample 104 it is desired that no gas bubbles are present in the transport path in between the CoS and the liquid sample. Undesired gas bubbles may result from immersing a suction pipe first into the reservoir 106 containing the CoS, pulling out the suction pipe from the reservoir 106 and subsequently immersing the suction pipe into the incubator 102. When swiveling the suction pipe between these two reservoirs and operating the pump 136 at that time, air or ambient gas may be sucked into the pipe 110 and thus the transport path.

The time period in phase ii. during which the liquid sample 104 is sucked into the transport path is designated with reference numeral 12 in FIG. 2. This is followed by time period 13 that is also part of the transport phase ii. in which further CoS is sucked into the transport path to move the liquid sample to the working electrode. In detail, time period 13 corresponds to transporting of the liquid sample to the working electrode and capturing of magnetic microparticles. This capturing is possible since said liquid sample is comprising a marking substance capable of effecting an electrochemiluminescence reaction to be detected as the electrochemiluminescence excitation, wherein said complex is bound to the magnetic microparticles. The capturing is comprising attracting the microparticles by a magnetic field thereby depositing the microparticles on a surface of the working electrode. Thus, time period 13 comprises taking up the liquid sample into the transport path and transporting the liquid sample to the working electrode by subsequently taking up the CoS into the transport path.

Here it is desired to have a gas bubble in between the CoS and the liquid sample when switching from taking up the liquid sample to taking up the CoS, i.e., at the transition between time period 12 and time period 13. The gas bubble may result from sucking air or ambient gas into the suction pipe when swiveling the suction pipe between the incubator 102 and the reservoir 106 for these liquids and operating the pump 136 at that time.

A major benefit of having the gas bubble in between the liquid sample and the CoS is that by moving the gas bubble over the working electrode a clear separation between liquid sample and CoS is ensured. Thus, an unwanted mixture of liquid sample and CoS is avoided.

Another reason for a gas bubble in between the CoS and the liquid sample when transitioning from time period 12 to time period 13 is as follows: well known to the system are the time points at which the suction of the liquid sample and the suction of the gas started. Further known as information is the velocity at which the liquid sample is transported in the transport path, as well as the geometric dimensions of the transport path. By determining the exact time point at which the air bubble arrives at a certain location in the transport path, as well as the information, the total volume of liquid sample that was taken into the transport path can be calculated.

As described above, the PMT 126 can detect the coupled light. For example, from the time point at which a variation of the intensity of the coupled light is detected the beginning of the gas bubble can be determined. This is because the gas bubble has different light diffraction and light transmission properties than the liquid sample.

Next, in block 306 (phase iv) the voltage source 122 is controlled to apply the pulse 15 onto the working electrode for excitation of the luminescence such that the measurement signal 130 results.

The measurement signal 130 is acquired by sampling the output of the photomultiplier 126 over a given period of time, such as 0.8 second before applying the pulse and 1.2 seconds after application of the pulse by the voltage source 122, for time-resolved measuring of the luminescence.

During the excitation of the luminescence the light source 204 is turned off to avoid any disturbing of the luminescence measurement.

The data samples that constitute the measurement signal 130 are stored within the memory 140 of the control unit 132 and the program module 148 is started for evaluation of the acquired measurement signal 130 for obtaining the concentration of the analyte.

Next, in block 308 (phase v) the pump 136 is controlled by the control unit 132 for removing the liquid from the conduit 114 and regeneration of the measuring cell 108. This phase v comprises taking up a cleaning solution from a reservoir 107 into the transport path. A valve 109 may be used to selectively couple the transport path to the reservoir 106, the incubator 201 and the reservoir 107. When switching from phase iv. to phase v. the measuring cell and thus the transport path still comprises the CoS. In order to more effectively clean the working electrode, again a gas may be sucked into the transport path for forming a gas bubble separating the CoS from the cleaning solution. The cleaning solution is taken up from a respective reservoir and the gas bubble may result from swiveling the suction pipe between the two reservoirs (CoS and cleaning solution) for these liquids and operating the pump 136 at that time when the suction pipe is located, e.g., in ambient air outside the two reservoirs. Here, the gas bubble again serves a clear separation between the two liquids CoS and cleaning solution thus avoiding a mixture of the two liquids and therefore a more efficient cleaning action of the 'pure' cleaning solution.

Designated by reference numerals 16 are various current pulses measured in between the working electrode and the counter electrode. These current pulses are the result of multiple optional gas bubbles transiting the measuring cell. For example, the multiple gas bubbles can be added to the cleaning solution itself in phase v. The multiple gas bubbles mechanically favor the removal of unwanted substances from the working electrode since each gas bubble provides an air-liquid interface which imposes a mechanical force onto the working electrode when being moved over the working electrode. As a result of the movement of the gas bubbles over the working electrode the current pulses in the current applied in between the working electrode and the counter electrode are measured.

During time period 17 CoS is taken up again into the transport path for preparing the transport path for the subsequent repetition of the conditioning (step 300 and phase i.). Again in order to avoid a mixture of the cleaning solution and the CoS, a gas bubble is used to separate the cleaning solution and the subsequently uptaken CoS. By generally avoiding a mixture of liquids and separating the liquids by a gas bubble, the required amount of liquids is minimized due to 'clean' interfaces between the liquids.

An optional washing step (block 304 and phase iii) in between the capturing (block 302) and measuring (block 306) may be performed in order to ensure that the marking substance not bound to magnetic microparticles which are not yet attached to the magnet are removed prior to performing the ECL measurement in block 306.

During any of the above described phases, the presence, non-presence and time point of presence of air bubbles, as well as the volume of liquids confined by the air bubbles, can be determined using the light source 204 and the measurement principles discussed above. Depending on the outcome of the measurements of the coupled light, ECL measurements can be flagged with respective measurement states indicating the outcome of the measurements of the coupled light. By means of the display 152, the measurement state can also be provided, as well as any additional information indicating for example an interpretation of the measurement state like 'valve defect' or 'liquid sample volume too small', etc.

In case the measurement state is provided in accordance with a predefined repetition pattern for multiple ones of the liquid sample, the processor 144 may also stop the operation of the measuring cell. For example, in case the repetition pattern is that the same error 'liquid sample volume too small' occurs for every sample, this corresponds to a systematic error and may be interpreted as sucking gas into the transport path during aspiration of the liquid sample. This may also be indicated using the display 152.

Figure 4:
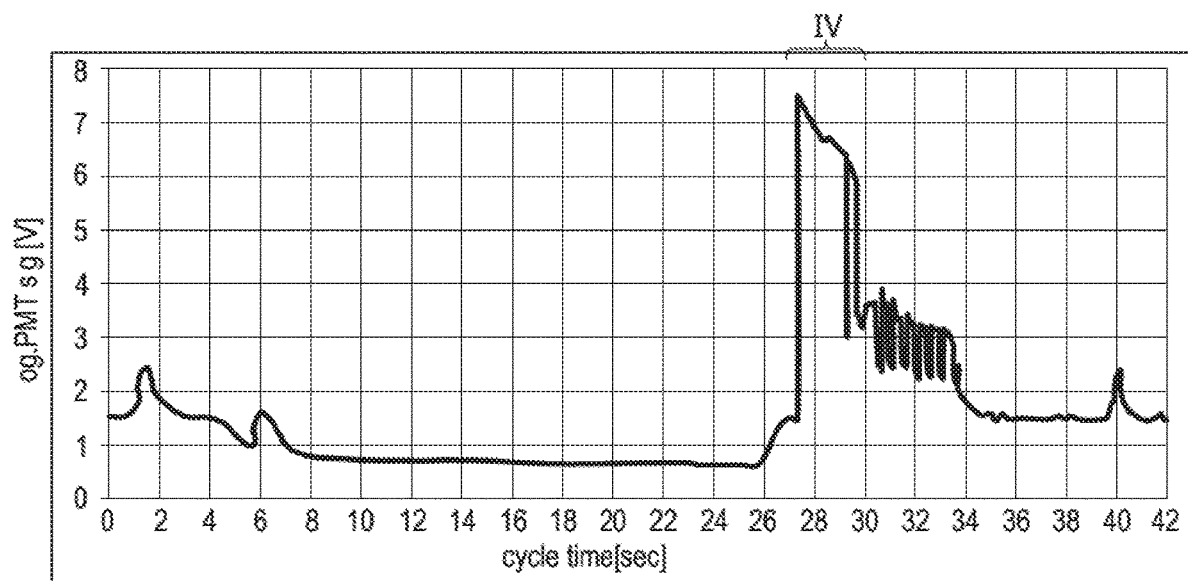
FIG. 4 shows PMT (photo multiplier tube) measurement results over the measurement cycle when the light source is turned off.

FIG. 4 is a diagram illustrating the PMT signal during the whole measurement cycle with the light source being turned off. During phase iv, the ECL signal is clearly visible.

Figure 5:
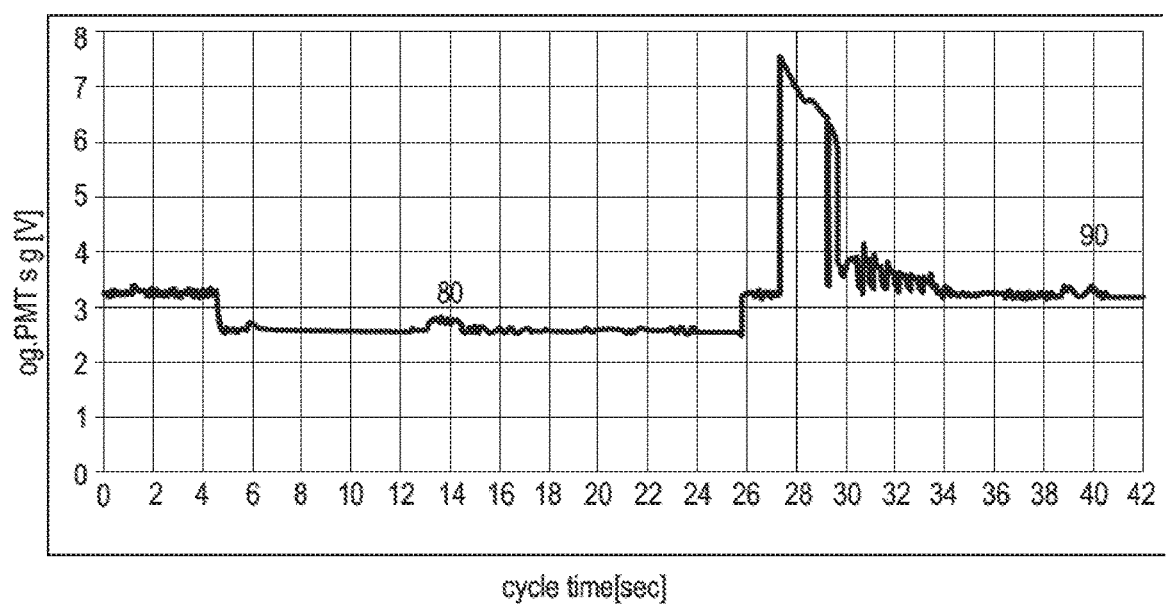

During the measurement of the PMT signal as shown in the diagram of FIG. 5, the light source was driven as an LED constantly with a current of 4 mA. As a consequence, the total signal level of detected light intensity is shifted up.

Due to a coupling of the light into the transport path, a change in the optical properties of the transport path is visible at the positions indicated by reference numerals 80 and 90. Reference numeral 80 hereby corresponds to the presence of an air bubble in between the liquid sample and the CoS at a transition from time period 12 to time period 13 (phase ii). Position 90 corresponds to an air bubble in between the cleaning solution and the subsequently taken up CoS, i.e., at the transition from phase v to i.

Figure 6:
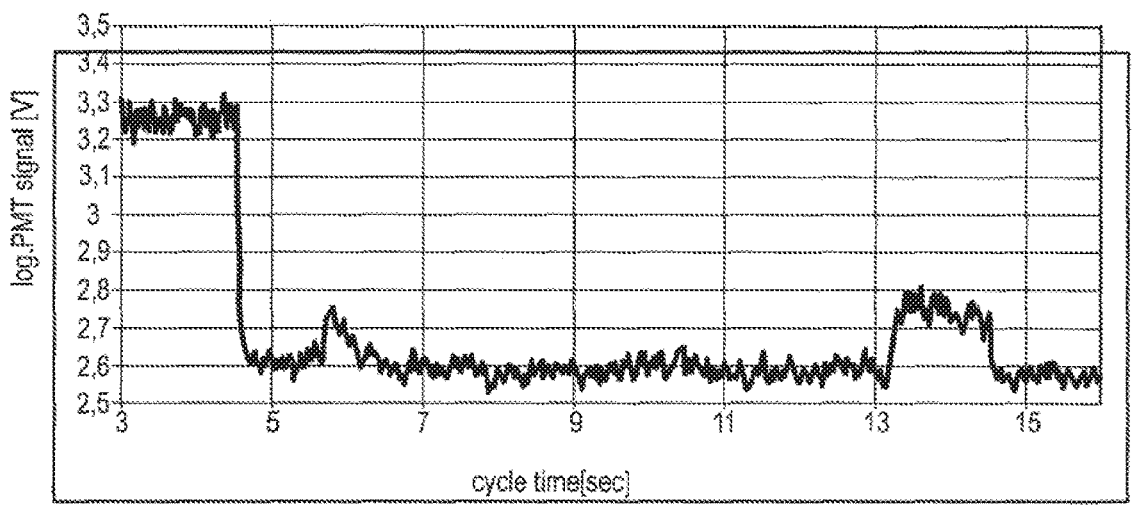
FIG. 6 shows PMT measurement results over a part of the measurement cycle when the light source is turned on and for an incubate size of 160 µl.
Figure 7:
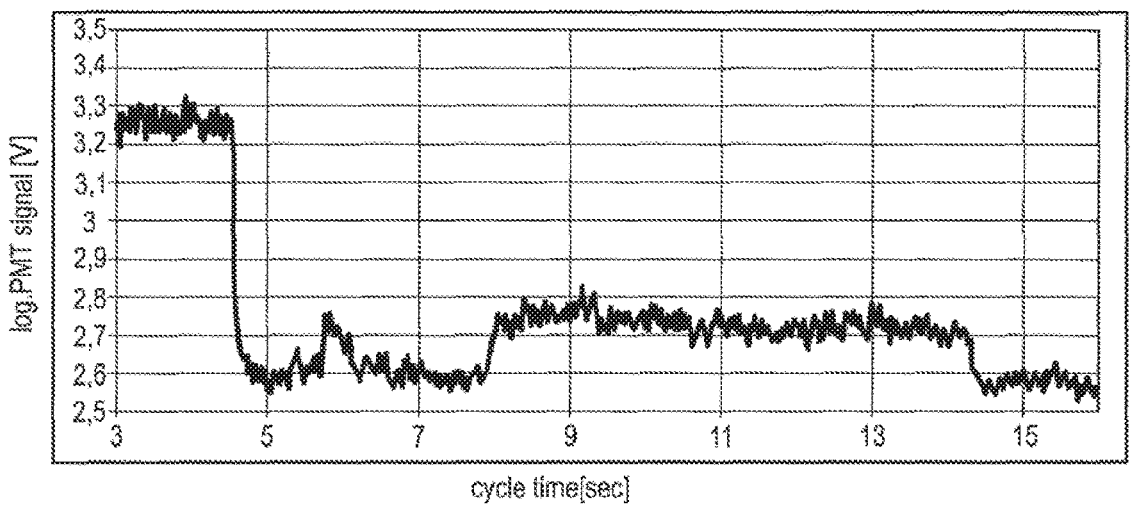
FIG. 7 shows PMT measurement results over a part of the measurement cycle when the light source is turned on and for an incubate size of 0 µl.

FIGS. 6 and 7 show different PMT measurement results over a part of the measurement cycle when the light source is turned on. In FIG. 6 an incubate size of 160 µl was used, whereas for FIG. 7 the incubate size was 0 µl. In both cases, the aspiration of the incubate (or the non-aspiration of the incubate) was terminated by an air bubble sucked into the transport path. As can be seen from FIG. 6, during the cycle due to the permanent presence of the incubate in the transport path it takes about 13 seconds until the air bubble arrives in the transport path and changes the optical properties of the transport path in such a manner, that the PMT signal is changed. This corresponds to an increase in the PMT signal intensity starting at around 13 seconds.

In contrast thereto, in case no incubate was aspirated into the transport path and the air bubble is immediately injected into the transport path at the time point where normally the liquid sample (incubate) would have been aspirated into the transport path, the optical properties of the transport path are immediately changed. This is visible in FIG. 7 by an increase of the PMT signal intensity that already starts around 8 seconds of the cycle time.

By systematically varying the incubate volume and recording the arrival time of the air bubble, a relationship between the incubate volume and the arrival time of the air bubble can be derived. The result is plotted in FIG. 8. For an incubate volume below 120 µl a linear dependency between the arrival time of the air bubble and the incubate volume can be identified. The arrival time of the air bubble gets into a 'saturation state' in case the incubate volume corresponds to the volume that can be fully taken up by the transport path.

Figure 8:
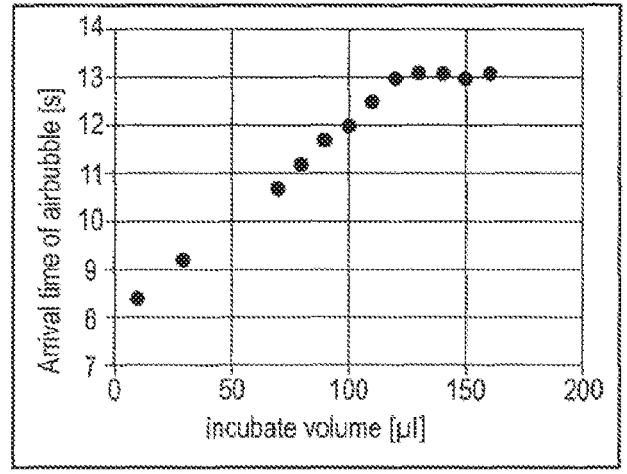
FIG. 8 shows the relationship between the incubate volume and the arrival time of the air bubble.

From FIG. 8 it becomes clear that by means of the PMT measurements of the light coupled into the transport path it is possible to determine the volume of the incubate that is taken up into the transport path. This provides a possibility for monitoring the correct operation of the system since this requires a minimum amount of incubate volume in order to operate correctly.

FIG. 9 is a decision table according to which a measurement state can be provided. In the column 'detection' only the presence or non-presence of gas bubbles at certain time points of the measurement cycle are listed. The next column 'problem' describes a deviation of the time point at which the gas bubble was detected from a reference or threshold value. Column 'occasional occurrence' lists the actions that are automatically taken by the system in case the problem is only occurring once or in an irregular manner. Finally, column 'systematic occurrence' lists the actions the system automatically takes in case of a systematic and regular occurrence of the problems.

Line number 1 corresponds to the scenario discussed above with respect to FIGS. 6, 7 and 8, i.e., the problem that the gas bubble between the liquid sample and the CoS arrives too early in the transport path. As was discussed above, this corresponds to a liquid sample volume that is too low in order to perform a correct ECL measurement. In case of an occasional occurrence of this problem, the resulting ECL measurement may be flagged in a corresponding manner indicating that the ECL measurement results may not be correct. Further, a user of the system may be informed about this problem using the above described display. In case of a systematic occurrence of this problem, an alarm may be provided by the system informing the user about this systematic problem and the measurement may be interrupted.

In line number 2, the same gas bubble between the liquid sample and the CoS may be analyzed regarding its arrival time in the transport path. In case the arrival time is too late, this indicates that the CoS volume flow is too low in the transport path. As a consequence, the respective measurement result of the ECL measurement may be flagged accordingly since this may indicate the problem that due to only a small movement of the liquid sample over the working electrode only a limited amount of analyte material may have been deposited on the working electrode. In case of a systematic occurrence, an alarm may be provided to the user of the system, the whole measurement may be interrupted and additionally by means of the display a user of the system may be informed by a possible malfunction that for example a seal is faulty, a valve is faulty or even the pump is faulty.

Line number 3 describes the detection of the gas bubble between the co-reactant and the cleaning solution. In case this gas bubble arrives too late in the transport path, this means that the cleaning solution volume flow is also too low. The same consequences regarding informing the user in case of occasional or systematic occurrence may be performed as discussed regarding the line number 2.

Line number 4 corresponds to the gas bubble of cleaning, i.e., the scenario in which during application of the current pulses 16 multiple air bubbles are moved over the working electrode. Again, in case the gas bubble of these multiple gas bubbles are arriving too late in the transport path, this has the same consequences as described before regarding line number 3.

Line number 5 relates to a gas bubble that is located between the cleaning solution and the CoS. In case this gas bubble arrives too late in the transport path, again this means that the CoS solution volume flow is too low and the same consequences regarding occasional and systematic occurrence are provided as discussed above regarding lines number 2, 3 and 4.

Finally, line number 6 relates to the scenario in which a gas bubble is detected in between the co-reactant and the liquid sample. As was discussed above, it may not be desired at all to have a gas bubble in between the co-reactant and the liquid sample. Therefore, in case the problem occurs that a gas bubble is detected, even though no gas bubble was expected, again the system provides respective information to the user of the system by flagging of a respective ECL measurement result, providing a warning. In case of a systematic occurrence, an alarm may be provided, including a possible interruption of ECL measurements and the indication of a possible malfunction of a faulty valve.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-ft DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present disclosure. Computer executable code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described with reference to flowchart illustrations and/or block diagrams of methods, apparatus (systems) and computer program products according to embodiments of the disclosure. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

LIST OF REFERENCE NUMERALS voltage profile 10
Time period 12
Time period 13
Time period 15
Time period 16
Time period 17
Time point 80
Time point 90
Analysis system 100
Incubator 102
Liquid 104
Reservoir 106
Reservoir 107
Measuring cell 108
Valve 109
Pipe system 110
Cell body 112
Conduit 114
Magnetic component 116
Actuator 118
Working electrode 120
Voltage source 122
Excitation area 124
Photomultiplier 126
Counter electrode 128
Measurement signal 130
Control unit 132
Container 134
Pump 136
Particle 138
Memory 140
Processor 144
Program module 146
Program module 148
Interface 150
Display 152
Window 156
Inlet 200
Outlet 202
Light source 204
Sealing 206
Window 212
Gas bubble 214

What is claimed is:

1. A method of monitoring an operation of detection of an analyte in a liquid sample using a measuring cell, the measuring cell comprising a working electrode for excitation of electrochemiluminescence in the liquid sample, an optical detector for detecting the excited electrochemiluminescence, the excitation and detection being performed in an electrochemiluminescence measurement cycle, the measurement cycle comprising transporting the liquid sample via a transport path to the working electrode using a support liquid, the method comprising:
coupling light of a light source into the transport path during part of the measurement cycle, the transport path forming a light guide between the light source and the optical detector;
detecting the coupled light by the optical detector;
analyzing the detected light regarding the presence state as to whether a gas bubble has been detected in the transport path, wherein the presence state is selected from the group consisting of: no gas bubble present in the transport path and/or gas bubble resent in the transport path;
comparing the presence state to a target state selected from the group consisting of no gas bubble expected in the transport path at the point in time and/or gas bubble expected in the transport path at the point in time;
determining whether the presence state deviates from the target state; and
if the presence state deviates from the target state, then providing a measurement state of the operation of detection.

2. The method of claim 1, the gas bubble separating the liquid sample and the support liquid.

3. The method of claim 1, in case of the presence of the gas bubble further comprising analyzing the detected light regarding a property of the gas bubble, the measurement state indicating a deviation of the property from a reference property by a predefined threshold.

4. The method of claim 3, the property being selected from anyone of: a time duration for which the gas bubble is detected, a time point at which the gas bubble is detected, an intensity of the detected coupled light.

5. The method of claim 4, the intensity of the detected coupled light being associated with a volume of the gas bubble, the reference property corresponding to a minimum volume of the gas bubble, the liquid sample and the support liquid being provided to the transport path through a pipe, the working electrode being contained in a measurement chamber being part of the transport path, the minimum volume of the gas bubble being selected such that at any location within the transport path and the pipe the gas bubble completely fills the cross section at this location of the transport path and the pipe, the cross section being perpendicular to the direction of transport of the liquid sample or the support liquid at this location.

6. The method of claim 1, the transport path being completely located within the measuring cell, the light source coupling the light into the transport path through a wall geometrically limiting the sides of the transport path.

7. The method of claim 6, the measuring cell comprising an integrated inlet port and an integrated outlet port, the working electrode being contained in a measurement chamber, the measurement chamber being in first fluid connection with the inlet port and the outlet port, the first fluid connection and the measurement chamber forming the transport path, the inlet port being adapted for receiving a pluggable pipe in second fluid connection with a reservoir containing the liquid sample.

8. The method of claim 1, further comprising:
light source being integrated in the measuring cell and/or the light source being turned off during the detection of the excited electrochemiluminescence.

9. The method of claim 1, the providing of the measurement state comprising displaying the measurement state on a display coupled to the measuring cell.

10. The method of claim 1, wherein in case the measurement state is provided in accordance with a predefined repetition pattern for multiple ones of the liquid sample, the method further comprises stopping the operation of the measuring cell.

11. The method of claim 1, the measurement cycle comprising any one of the following:
- a first phase for conditioning of the working electrode without the liquid sample using an auxiliary solution as the support liquid, the first phase comprising taking up the auxiliary solution as the support liquid into the transport path,
- a second phase for the transporting of the liquid sample to the working electrode and capturing of magnetic microparticles, said liquid sample comprising a marking substance capable of effecting an electrochemiluminescence reaction to be detected as the electrochemiluminescence excitation, said complex further being bound to the magnetic microparticles, said capturing comprising attracting the microparticles by a magnetic field thereby depositing the microparticles on a surface of said working electrode, the second phase comprising taking up the liquid sample into the transport path and transporting the liquid sample to the working electrode by subsequently taking up the auxiliary solution as the support liquid into the transport path,
- a third phase for washing of the working electrode after the capturing and before the excitation of the electrochemiluminescence, said third phase being adapted to remove unbound complexes from the working electrode, the washing being performed using the auxiliary solution as the support liquid, the third phase comprising taking up the auxiliary solution as the support liquid into the transport path,
- a fourth phase for performing the electrochemiluminescence measurement on the sample,
- a fifth phase for cleaning of the working electrode with a cleaning solution, the fifth phase comprising taking up the cleaning solution into the transport path,
- the target state regarding the presence of a gas bubble separating the liquid sample and the support liquid being any one of the following:
- no gas bubble in between the support liquid and the liquid sample when switching from the first phase to the second phase,
- a gas bubble in between the support liquid and the liquid sample when switching from the second phase to the third phase,
- a gas bubble in between the support liquid and the cleaning solution when switching from the fourth phase to the fifth phase,
- a gas bubble in between the cleaning solution and the support liquid when switching from the fifth phase to the first phase for a subsequent run of the measurement cycle.

12. The method of claim 1, the gas comprising anyone of the following: air, inert gas, nitrogen.

13. The method of claim 1, the transporting of the liquid sample via the transport path to the working electrode using the support liquid being performed using a suction device adapted for sucking the liquid sample and the support liquid into the transport path.

14. The method of claim 1 further comprising:
the transporting of the liquid sample via the transport path being performed at a flow velocity within a range of about 5 to about 1000 µl/s, and/or
the volume of the gas bubble being within a range of about 5 to about 100 µl.

15. The method of claim 1 further comprising:
the transporting of the liquid sample via the transport path being performed at a flow velocity within a range of about 20 to about 400 µl/s, and/or
the volume of the gas bubble being within a range of about 10 to about 30 µl.

16. An apparatus for monitoring an operation of detection of an analyte in a liquid sample using a measuring cell, the apparatus comprising the measuring cell, the measuring cell comprising a working electrode for excitation of electrochemiluminescence in the liquid sample and an optical detector for detecting the excited electrochemiluminescence and a processing unit for determining the analyte from the detected electrochemiluminescence, the apparatus being adapted for performing the excitation and detection in an electrochemiluminescence measurement cycle, the measurement cycle comprising transporting the liquid sample via a transport path to the working electrode using a support liquid, the apparatus comprising a processor and a memory, the memory comprising computer executable instructions, execution of the instructions by the processor causing the apparatus to:
- coupling light of a light source into the transport path during part of the measurement cycle, the transport path forming a light guide between the light source and the optical detector,
- detecting the coupled light by the optical detector,
- analyzing the detected light regarding the presence state as to whether a gas bubble has been detected in the transport path, wherein the presence state is selected from the group consisting of: no gas bubble present in the transport path and/or gas bubble present in the transport path,
- comparing the presence state to a target state selected from the group consisting of no gas bubble expected in the transport path at the point in time and gas bubble expected in the transport path at the point in time.

17. The method of claim 1 in which the presence state is no gas bubble present and the target state is gas bubble expected.

18. The method of claim 1 in which the presence state is gas bubble present and the target state is no gas bubble expected.

19. The method of claim 18, the gas bubble separating the liquid sample and the support liquid.

20. The method of claim 1 in which the presence state is gas bubble present and the target state is either gas bubble expected or no gas bubble expected.

21. The method of claim 20 and which further comprises:
analysing the detected light regarding a property of the detected gas bubble;
comparing the property with a reference property; and
if the property deviates from the reference property by a predefined threshold, providing a measurement state of the operation of detection.

22. The method of claim 21 in which the property is the time the gas bubble arrived at the location and the reference property is the time the gas bubble was expected to arrive at the location.

23. The method of claim 21 in which the property is the time the gas bubble left the location and the reference property is the time the gas bubble was expected to leave the location.

24. The method of claim 21 in which the property is the size of the gas bubble passing the location and the reference property is the size of the gas bubble expected to pass the location.

25. A method of monitoring an operation of detection of an analyte in a liquid sample using a measuring cell, the measuring cell comprising a working electrode for excitation of electrochemiluminescence in the liquid sample, an optical detector for detecting the excited electrochemiluminescence, the excitation and detection being performed in an electrochemiluminescence measurement cycle, the measurement cycle comprising transporting the liquid sample via a transport path to the working electrode using a support liquid, the method comprising:
  coupling light of a light source into the transport path during part of the measurement cycle, the transport path forming a light guide between the light source and the optical detector;
  detecting the coupled light by the optical detector;
  analyzing the detected light regarding the presence of a gas bubble in the transport path;
  providing a measurement state in case the result of the analysis deviates from a target state regarding the presence of a gas bubble in the transport path, wherein the target state is of no gas bubble present in the transport path and gas bubble present in the transport path;
  the measurement cycle comprising any one of the following:
    a first phase for conditioning of the working electrode without the liquid sample using an auxiliary solution as the support liquid, the first phase comprising taking up the auxiliary solution as the support liquid into the transport path,
    a second phase for the transporting of the liquid sample to the working electrode and capturing of magnetic microparticles, said liquid sample comprising a marking substance capable of effecting an electrochemiluminescence reaction to be detected as the electrochemiluminescence excitation, said complex further being bound to the magnetic microparticles, said capturing comprising attracting the microparticles by a magnetic field thereby depositing the microparticles on a surface of said working electrode, the second phase comprising taking up the liquid sample into the transport path and transporting the liquid sample to the working electrode by subsequently taking up the auxiliary solution as the support liquid into the transport path,
    a third phase for washing of the working electrode after the capturing and before the excitation of the electrochemiluminescence, said third phase being adapted to remove unbound complexes from the working electrode, the washing being performed using the auxiliary solution as the support liquid, the third phase comprising taking up the auxiliary solution as the support liquid into the transport path,
    a fourth phase for performing the electrochemiluminescence measurement on the sample,
    a fifth phase for cleaning of the working electrode with a cleaning solution, the fifth phase comprising taking up the cleaning solution into the transport path,
  the target state regarding the presence of a gas bubble separating the liquid sample and the support liquid being any one of the following:
    no gas bubble in between the support liquid and the liquid sample when switching from the first phase to the second phase,
    a gas bubble in between the support liquid and the liquid sample when switching from the second phase to the third phase,
    a gas bubble in between the support liquid and the cleaning solution when switching from the fourth phase to the fifth phase,
    a gas bubble in between the cleaning solution and the support liquid when switching from the fifth phase to the first phase for a subsequent run of the measurement cycle.

* * * * *